US012790632B2

(12) United States Patent
Aitken et al.

(10) Patent No.: US 12,790,632 B2
(45) **Date of Patent: *Nov. 10, 2026**

(54) **METHOD FOR DETECTING DORMANT OR CELL WALL DEFICIENT *MYCOBACTERIUM* SPECIES AND A METHOD AND MEDIUM FOR THE GROWTH PROMOTION OF DORMANT OR CELL WALL DEFICIENT FORMS OF *MYCOBACTERIUM* SPECIES**

(71) Applicant: Otakaro Pathways Limited, Christchurch (NZ)

(72) Inventors: John Milford Aitken, Christchurch (NZ); Khoi Phan, Wellington (NZ)

(73) Assignee: Otakaro Pathways Limited, Christchurch (NZ)

( * ) Notice: Subject to any disclaimer, the term of this patent is extended or adjusted under 35 U.S.C. 154(b) by 939 days.

This patent is subject to a terminal disclaimer.

(21) Appl. No.: 17/430,334

(22) PCT Filed: Feb. 28, 2020

(86) PCT No.: PCT/IB2020/051703
§ 371 (c)(1),
(2) Date: Aug. 12, 2021

(87) PCT Pub. No.: WO2020/178685
PCT Pub. Date: Sep. 10, 2020

(65) Prior Publication Data

US 2022/0127657 A1 Apr. 28, 2022

(30) Foreign Application Priority Data

Mar. 1, 2019 (NZ) ........................................ 751215

(51) Int. Cl.
*C12Q 1/04* (2006.01)
*A61B 5/00* (2006.01)
(Continued)

(52) U.S. Cl.
CPC ............ *C12Q 1/045* (2013.01); *A61B 5/4848* (2013.01); *C12N 1/20* (2013.01); *A61B 5/15* (2013.01); *A61B 10/02* (2013.01)

(58) Field of Classification Search
CPC ....... G01N 2333/35; C12Q 1/045; C12N 1/20
See application file for complete search history.

(56) References Cited

U.S. PATENT DOCUMENTS 6,168,930 B1 * 1/2001 Horn ...................... C12Q 1/045 435/244
11,485,992 B2 * 11/2022 Aitken ..................... G01N 1/30
(Continued)

FOREIGN PATENT DOCUMENTS

| | | | |
|---|---|---|---|
| EP | 0489392 A2 * | 3/1991 |
| WO | WO 2017103799 | 6/2017 |
| WO | WO 2018176066 | 9/2018 |

OTHER PUBLICATIONS

Flournoy D, Twilley J. Modified Middlebrook 7H9 broth for the rapid detection of mycobacteria. Clin Lab Sci. 2001 Spring; 14(2):85-8. PMID: 15625980. (Year: 2001).*
(Continued)

*Primary Examiner* — Manjunath N Rao
*Assistant Examiner* — Qing Xu
(74) *Attorney, Agent, or Firm* — LaMorte & Associates PC

(57) ABSTRACT

A method for detecting, in a blood or tissue sample, dormant or cell wall deficient *Mycobacterium* species, said method including using a Ziehl Neelsen stain as hereinbefore defined, which includes treating the sample with carbol fuchsin, followed by treating the sample with a decolouriser and with a counter stain.

12 Claims, 9 Drawing Sheets

(51) Int. Cl.
*C12N 1/20* (2006.01)
*A61B 5/15* (2006.01)
*A61B 10/02* (2006.01)

(56) References Cited

U.S. PATENT DOCUMENTS

2003/0147861 A1* 8/2003 Watson .................. A61P 17/06 424/248.1
2014/0056952 A1* 2/2014 Losick .................. C07C 211/11 514/183
2014/0271719 A1* 9/2014 Talaat ................ C12N 15/1136 435/7.1
2015/0252402 A1* 9/2015 Swarts ..................... C07H 3/04 435/100
2016/0168614 A1 6/2016 Hunt
2017/0022542 A1 1/2017 Zhang et al.
2020/0199523 A1* 6/2020 Love ........................ C12N 1/16

OTHER PUBLICATIONS

Saleh A Naser, George Ghobrial, Claudia Romero, John F Valentine, Culture of *Mycobacterium avium* subspecies *paratuberculosis* from the blood of patients with Crohn's disease, The Lancet, 364(9439), 2004, p. 1039-1044, ISSN 0140-6736, https://doi.org/10.1016/S0140-6736(04)17058-X (Year: 2004).*

Martínez-Martínez, Yazmin Berenice, Herminia Guadalupe Martínez-Rodríguez, and Salvador Luis Said-Fernández. "Conventional and Molecular Diagnosis of Drug-Sensitive and Drug-Resistant Pulmonary Tuberculosis." *Mycobacterium*—Research and Development. IntechOpen, 2018. (Year: 2018).*

BioGnost; Feb. 2017; www.biognost.com/wp-content/uploads/2020/02/Gabbett-reagent-IFU-V2-EN2.pdf (Year: 2017).*

Prince; 2018; https://princesterilization.com/difference-between-moist-heat-sterilization-dry-heat-sterilization/ (Year: 2018).*

Selleckchem; 2017; https://web.archive.org/web/20171129040428/https://www.selleckchem.com/qa.html (Year: 2017).*

Baker JJ, Abramovitch RB. Genetic and metabolic regulation of *Mycobacterium tuberculosis* acid growth arrest. Sci Rep. Mar. 8, 2018;8(1):4168. doi: 10.1038/s41598-018-22343-4. PMID: 29520087; PMCID: PMC5843633. (Year: 2018).*

Boyd MA, Tennant SM, Melendez JH, Toema D, Galen JE, Geddes CD, Levine MM. Adaptation of red blood cell lysis represents a fundamental breakthrough that improves the sensitivity of *Salmonella* detection in blood. J Appl Microbiol. May 2015;118(5):1199-209. doi: 10.1111/jam.12769. (Year: 2015).*

Lovering AL, Safadi SS, Strynadka NC. Structural perspective of peptidoglycan biosynthesis and assembly. Annu Rev Biochem. 2012;81:451-78. doi: 10.1146/annurev-biochem-061809-112742. (Year: 2012).*

Sarathy JP, Lee E, Dartois V. Polyamines inhibit porin-mediated fluoroquinolone uptake in mycobacteria. PLoS One. Jun. 3, 2013;8(6):e65806. doi: 10.1371/journal.pone.0065806. (Year: 2013).*

Rao, "Bacterial Culture Media," downloaded Dec. 19, 2024 from < https://microrao.com/micronotes/culture_media.pdf> (Year: 2006).*

Belishe et al., Mycobacteria Protocols. 2nd Edition, Parish and Brown, Chapter 1, Humana Press. (Year: 2008).*

Brzostek et al., J. Bacterio., 2009, 191(21):6584-6591 (Year: 2009).*

Harris et al., J Vet Diagn Invest, 2005 17:554-560 (Year: 2005).*

Elkins et al., Current Protocols in Immunology, 2011, 14.25.1-14.25.13 (Year: 2011).*

Wikipedia printout of Middlebrook 7H9 Broth, retrieved from URL: https://en.wikipedia.org/wiki/Middlebrook_7H9_Broth, on Jul. 1, 2025 (Year: 2025).*

Safety Data Sheet: TB Decolorizer (3% Acid Alcohol) [retrieved from the internet on Apr. 22, 2020] URL: https//www.fishersci.com/shop//msdsproxy?productName=R40206&productDescription=TB+DECOLORIZER+3%2525+ACID+A+1PK&catNo=R40206&vendorId=W00040817&storied==10652 Published on Oct. 25, 2017.

Aung, K.J.M. et al., "Hydrochloric vs. sulphuric acid in water for Ziehl-Neelsen staining of acid-fast bacilli", The International Journal of Tuberculosis and Lung Disease. 2011, vol. 15, pp. 955-958.

Jiminez, J. et al., 'Animal models to study acute and chronic intestinal inflammation in mammals'. Gut Pathogens. 2015, vol. 7, pp. 1-31.

Heppler. B. et al., The ethics of research involving animals, Nuffield Council on Bioethics. 2005, ISBN 1 904384 10 2, pp. 107-118.

Okechukwu, L. 'Introductory Chapter: Animal Models for Human Human Diseases, a Major Contributor to Modem Medicine', IntechOpen. 2018, ISBN 978 1 78923 165 6, pp. 3-9.

Seiler P. et al., 'Cell-Wall Alterations as an Attribute of *Mycobacterium tuberculosis* in Latent Infection', The Journal of Infectious Diseases. 2003, vol. 188, pp. 1326-1331.

Noortje Dannenberg et al., Mycobacteria form viable cell wall-deficient cells that are undetectable by conventional diagnostics, Institute of Biology, Leiden University, Sylviusweg 72, 2333 BE Leiden, The Netherlands, Posted on Internet Nov. 16, 2022, available at https://doi.org/10.1101/2022.11.16.516772.

Saleh Naser et al., *Mycobacterium avium* subspecies *paratuberculosis* causes Crohn's disease in some inflammatory bowel disease patients, World Journal of Gastroenterology, Jun. 21, 2014, vol. 20, Issue 23, available at www.wjgnet.com.

N. Dannenberg et al., "Mycobacteria form viable cell wall-deficient cells that are undetectable by conventional diagnostics," Microbiology, preprint, Nov. 2022. doi: 10.1101/2022.11.16.516772.

A. Csillag, "Spore formation and 'dimorphism' in the mycobacteria", J Gen Microbiol, vol. 26, pp. 97-109, Sep. 1961, doi: 10.1099/00221287-26-1-97.

M. Daffé and H. Marrakchi, "Unraveling the Structure of the Mycobacterial Envelope," Microbiol Spectr, vol. 7, No. 4, Jul. 2019, doi: 10.1128/microbiolspec.GPP3-0027-2018.

M. S. Jurkowitz et al., "*Mycobacterium tuberculosis* encodes a YhhN family membrane protein with lysoplasmalogenase activity that protects against toxic host lysolipids," J Biol Chem, vol. 298, No. 5, p. 101849, May 2022, doi: 10.1016/j.jbc.2022.101849.

R. Chiodini, H. J Van Kruiningen, W. R Thayer, R. S Merkal, and J. Coutu, "Possible role of mycobacteria in inflammatory bowel disease., I. An unclassified *Mycobacterium* species isolated from patients with with Crohn's disease", vol. 29. 1985. doi: 10.1007/BF01317078.

R. J. Chiodini, H. J. Van Kruiningen, W. R. Thayer, and J. A. Coutu, "Spheroplastic phase of mycobacteria isolated from patients with Crohn's disease.," Journal of Clinical Microbiology, vol. 24, No. 3, Art. No. 3, 1986.

W. R. Burnham, J. E. Lennard-Jones, J. L. Stanford, and R. G. Bird, "Mycobacteria as a possible cause of inflammatory bowel disease", Lancet, vol. 2, No. 8092 Pt 1, pp. 693-696, Sep. 1978, doi: 10.1016/s0140-6736(78)92699-5.

S. Chandrasekhar and S. Ratnam, "Studies on cell-wall deficient non-acid fast variants of *Mycobacterium tuberculosis*," Tubercle and Lung Disease, vol. 73, No. 5, pp. 273-279, Oct. 1992, doi: 10.1016/0962-8479(92)90132-4.

R. J. Chiodini, H. J. Van Kruiningen, W. R. Thayer, and J. A. Coutu, "Spheroplastic phase of mycobacteria isolated from patients with with Crohn's disease.", Journal of Clinical Microbiology, vol. 24, No. 3, pp. 357-363, 1986.

M. M. Estevinho et al., "Viable *Mycobacterium avium* subsp. *paratuberculosis* Colonizes Peripheral Blood of Inflammatory Bowel Disease Patients," Microorganisms, vol. 11, No. 6, Art. No. 6, Jun. 2023, doi: 10.3390/microorganisms11061520.

V. Beran, M. Havelkova, J. Kaustova, L. Dvorska, and I. Pavlik, "Cell wall deficient forms of mycobacteria: a review," Veterinarni Medicina-Praha-, vol. 51, No. 7, Art. No. 7, 2006.

J. T. Kuenstner et al., "Presence of Infection by *Mycobacterium avium* subsp. *paratuberculosis* in the Blood of Patients with Crohn's Disease and Control Subjects Shown by Multiple Laboratory Culture and Antibody Methods," Microorganisms, vol. 8, No. 12, Art. No. 12, Dec. 2020, doi: 10.3390/microorganisms8122054.

Gaurav Agrawal, Thomas J. Borody, and John M. Aitken, "Mapping Crohn's Disease Pathogenesis with *Mycobacterium paratuberculosis*:

(56) References Cited

OTHER PUBLICATIONS

A Hijacking by a Stealth Pathogen", Digestive Diseases and Sciences, https://doi.org/10.1007/s10620-024-08508-4, Published online Jun. 19, 2024.
Anje A. teVelde, "Putting Crohn's Disease on the MAP: Potential Contribution of a Stealth Pathogen", Digestive Diseases and Sciences, https://doi.org/10.1007/s10620-024-08503-9, Published online Jun. 20, 2024.

* cited by examiner thickened outer membrane
A

METHOD FOR DETECTING DORMANT OR CELL WALL DEFICIENT *MYCOBACTERIUM* SPECIES AND A METHOD AND MEDIUM FOR THE GROWTH PROMOTION OF DORMANT OR CELL WALL DEFICIENT FORMS OF *MYCOBACTERIUM* SPECIES

TECHNICAL FIELD

The present invention relates to a method for detecting dormant or cell wall deficient *Mycobacterium* species, and to a method for promoting the growth of dormant forms or cell wall deficient *Mycobacterium* species, and to a culture medium for use in this method.

The method and medium of the present invention have been developed with especial reference to detecting and/or promoting the growth of cell-wall deficient and/or dormant forms of *Mycobacterium* species which are present in human beings, and most especially to *Mycobacterium avium* ssp paratuberculosis, and therefore will be described with particular reference to this application. However, it is envisaged that the methods and medium of the present invention could be used to detect and/or promote the growth of dormant forms or cell wall deficient forms of a range of *Mycobacterium* species, some of which are now believed to be associated with autoimmune and/or inflammatory diseases in human beings. Examples of such diseases include Crohn's disease, multiple sclerosis, regional pain syndrome, Alzheimer's disease sarcoidosis and rheumatoid arthritis.

The objective in promoting the growth of dormant forms of *Mycobacterium* species, and in particular the dormant form of *Mycobacterium avium* ssp paratuberculosis (MAP), is to make a positive identification of the presence in a sample of human blood or human tissue of the organism now believed to provide a biomarker i.e. to indicate the presence of Crohn's disease in the human being who provided the blood or tissue sample. The MAP organism has cell walls which are either partly or completely absent, and this makes the organism very hard to detect in a sample, because it is the cell walls which usually react to stains applied to the sample, and thus make the organism visible to inspection.

BACKGROUND ART

Any discussion of techniques as "background art" should not be taken as implying that these techniques are part of the common general knowledge in the field or that they are established techniques.

For many years, it has been widely accepted that to use a stain to detect the presence of a selected bacteria in a sample, the bacteria had to have a cell wall, because it was the cell wall which was believed to be coloured by the stain.

For example, the detection of *Mycobacterium tuberculosis* and *Mycobacterium leprae* was achieved using a Ziehl Neelsen stain (as hereinafter defined) which coloured the cell walls.

However, it is suspected that some mycobacteria to do not have well-defined cell walls; these are referred to as "cell wall deficient" bacteria. Also, if the bacteria are in a dormant stage, again the cell walls are not well defined.

This has presented considerable problems in the detection of some species of mycobacteria because the use of any of the range of standard stains does not provide a satisfactory result.

In particular, the detection of dormant or cell wall deficient mycobacteria in blood samples or in samples of macerated tissue (as opposed to solid tissue samples) has proved particularly difficult.

NZ patent application number 743000 discloses methods of culturing and detecting a biomarker by culturing a patient sample in a specified novel culture medium. The methods disclosed in that patent application have shown a considerable improvement in the difficult identification of the selected biomarkers.

DISCLOSURE OF INVENTION

An object of the present invention is the provision of a method for detecting a dormant or cell wall deficient *Mycobacterium* species and also to a method and medium for the growth promotion of cell-wall deficient and/or dormant forms of *Mycobacterium* species which provide an improved result compared to the methods disclosed in NZ application number 743000, and which can be used either as a replacement for those methods or as an addition to them.

The present invention provides a method for detecting, in a blood or tissue sample, dormant or cell wall deficient *Mycobacterium* species, said method including using a Ziehl Neelsen stain as hereinafter defined, which includes treating the sample with carbol fuchsin, followed by treating the sample with a decolouriser and with a counterstain.

Thus, the present invention provides a novel staining method which can be used to detect dormant or cell wall deficient *Mycobacterium* species in any of a blood sample, a macerated tissue sample or a solid tissue sample. However, for optimum results, it is preferred that for the detection of a dormant or cell wall deficient *Mycobacterium* species from a blood sample or a macerated tissue sample, that the culture medium and methods described below are used prior to staining, to increase the number of mycobacteria present, and thus improve the detection rate.

Preferably, before the Ziehl Neelsen stain is applied to a blood or macerated tissue sample, the sample is cultured to increase the number of dormant or cell wall deficient *Mycobacterium* species present. Preferably, the sample is cultured in a novel culture medium in accordance with the present invention, which is prepared as follows:—

A. A base medium is prepared from:

Middlebrook's 7H9 broth—5.9 grams/litre

Bacto nutrient broth—1.25 grams/litre glycerol—2.0 millilitres/litre sodium chloride 0-10.0 grams/litre;

the above ingredients are mixed together, made up to 1 litre with distilled water, and sterilised by heating; the sodium chloride may be added to the mixture before or after sterilisation;

B. A first additional preparation is made by mixing together the constituents listed below, stated in grams per litre of the final culture medium:—

| | |
|---|---|
| Bovine serum albumin | 1 gram to 20 gram |
| Dextrose | 0.5 gram to 20 gram |
| Sucrose | 1 gram to 25 gram |
| Tryptophan | 0.01 gram to 4 gram |
| Glutamic acid | 0.01 gram to 5 gram |
| L alanine | 0.01 gram to 5 gram |
| Oleic acid | 0.01 millilitres to 2 millilitres |

-continued

| | |
|---|---|
| L lysine | 0.01 gram to 5 gram |
| L asparagine | 0.01 gram to 5 gram |
| Vitamin B12 | 0.0125 gram to 1 gram |

C. A second additional preparation is made by mixing the constituents listed below, given in grams per litre of the final culture medium:—

| | |
|---|---|
| Isovitalex ® | 1 ml/L to 10 /L |
| Mycobactin J | 0.1 mg/L to 5 mg/L |
| PANTA ® | 15 per 200 |

The Isovitalex®, Mycobactin J, and PANTA® are added to normal saline, then dissolved and filtered for sterility;

D. Serum selected from the group consisting of: foetal calf serum; guinea pig blood serum, sheep blood serum, is prepared for use by inactivating the serum by heat treatment, and then filtering;

E. The final culture medium is prepared by mixing the base medium, and the first and second additional preparations to form a working medium and then said serum is added in a proportion 1%-10% by volume, to give the completed culture medium.

Preferably also, the first additional preparation also contains, per litre of the final culture medium:—

| | |
|---|---|
| Trehalose | 0.01 gram to 4 gram |
| D alanine | 0.01 gram to 5 gram |
| Putresceine | 0.01 gram to 5 gram |
| Cadavaerine | 0.01 gram to 0.5 gram |
| Cysteine | 0.01 gram to 0.5 gram |
| Sodium pyruvate | 0.01 gram to 10 gram |

As noted above, the culture medium must be sterile. To ensure this, the first additional preparation may be sterilised by passing the mixture through a 0.22 micron filter before mixing with the second additional preparation and the serum. Alternatively, the first and second additional preparations may be mixed together, mixed with the inactivated serum and with the base medium (which has already been heat sterilised), and the final culture medium is then sterilised by passing through a 0.22 micron filter.

In the most preferred form of the culture medium, the medium also contains egg yolk emulsion and/or cholesterol powder, as hereinafter described.

In one embodiment of the invention, the *Mycobacterium* species to be detected is a biomarker for an inflammatory disease or an autoimmune disease e.g. Crohn's disease.

The present invention further relates to the use of guinea pigs as an animal model for the diagnosis and/or testing of therapies for Crohn's disease.

In a preferred embodiment of the invention, a method for diagnosing Crohn's disease includes the steps of:

- taking blood or macerated tissue samples from one or more persons suffering from Crohn's disease;
- using a method as described below to culture said samples;
- feeding organisms from said cultured samples to one or more guinea pigs;
- monitoring said guinea pigs at predetermined intervals to confirm uptake of the disease by the guinea pigs;
- testing blood or tissue samples from the guinea pigs to confirm the presence of the biomarker for Crohn's disease.

A further preferred embodiment of the present invention relates to a method for testing therapies for Crohn's disease including the steps of:

- taking blood or macerated tissue samples from one or more persons suffering from Crohn's disease;
- using a method as described to culture said samples;
- feeding organisms from said cultured samples to a plurality of guinea pigs;
- monitoring said guinea pigs at predetermined intervals to confirm uptake of the disease by the guinea pigs;
- testing blood or tissue samples from the guinea pigs to confirm the presence of a biomarker for Crohn's disease;
- treating at least some of said guinea pigs with a selected therapy for Crohn's disease;
- evaluating said therapy at predetermined intervals by comparing the treated and nontreated guinea pigs.

The present invention further relates to a method of using a culture medium as set out above, said method including the steps of:

- obtaining a blood sample or a macerated tissue sample;
- inoculating the sample onto the culture medium;
- incubating the inoculated culture medium at 36.5-39 degrees centigrade for a predetermined period.

If the sample is a blood sample, then preferably prior to inoculating the sample onto the culture medium, the following steps are taken:

- citrating the sample with sodium citrate;
- centrifuging the sample;
- harvesting the buffy coat;
- inoculating the buffy coat into the culture medium.

Most preferably, after harvesting the buffy coat but before inoculating the buffy coat into the culture medium, the buffy coat is washed in distilled water, centrifuged, re-washed in distilled water, and re-centrifuged.

BRIEF DESCRIPTION OF DRAWINGS

By way of example only, preferred embodiments of the present invention are described in detail, with reference to the accompanying Figures, in which:—

Figure 1:
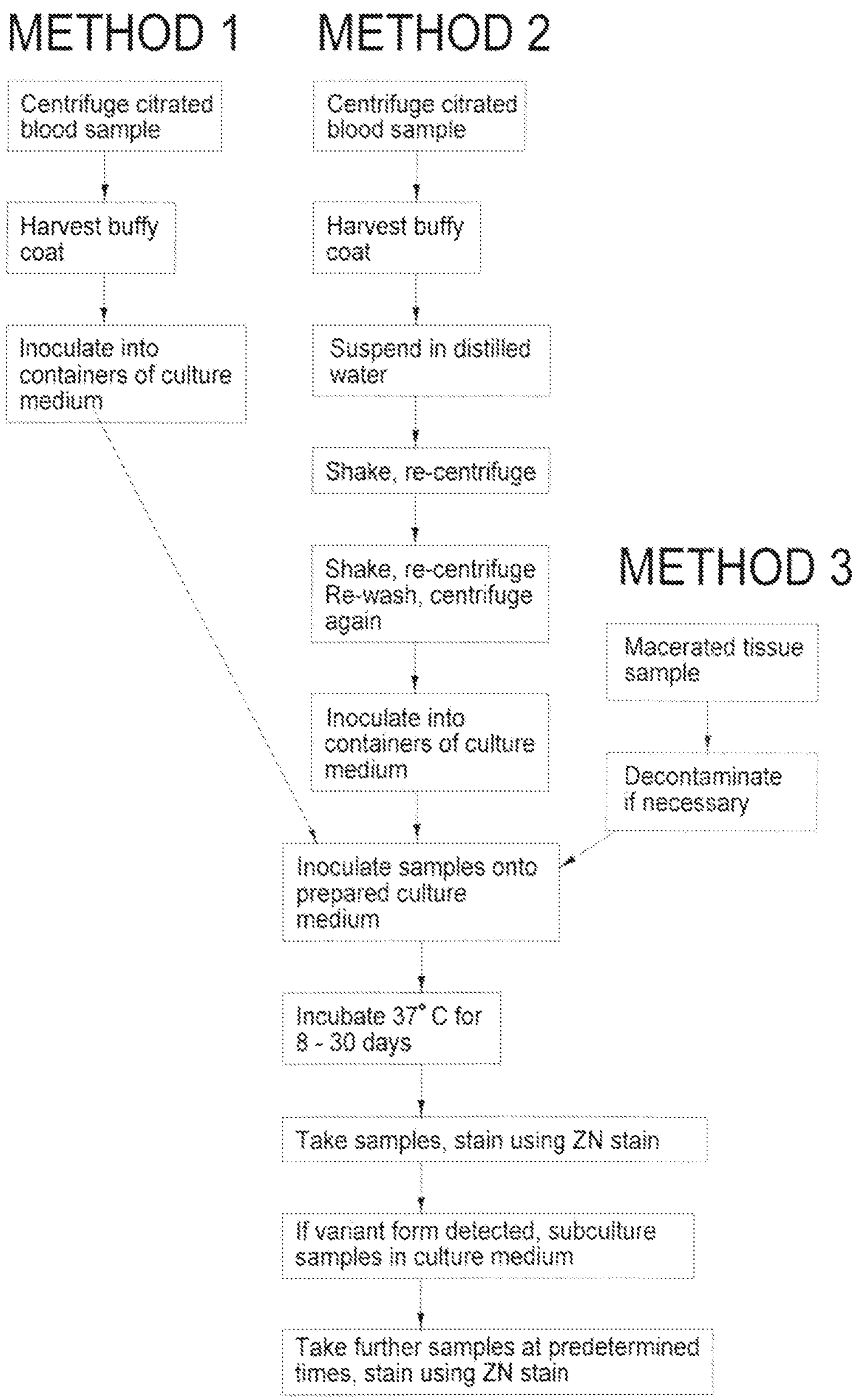
FIG. 1 is a flowchart showing the steps of the method of the present invention.

All of the photomicrographs are ×1000, oil immersion.

BEST MODE FOR CARRYING OUT THE INVENTION

Definitions

Middlebrook's 7H9 broth is a known proprietary nutrient broth.

Bacto nutrient broth is a known proprietary nutrient broth.

PANTA® is a commercially available antimicrobial preparation, which is an antimicrobial supplement containing polymyxin B, amphotericin B, nalidixic acid, trimethoprim and azlocillin.

The basic method of detecting dormant or cell wall deficient *Mycobacterium* species is to apply to a blood sample, a macerated tissue sample, or a solid tissue sample a Ziehl Neelsen stain as defined above. A detailed description of the staining methods and preparations used is given below; all three described staining methods have been found to detect dormant or cell wall deficient *Mycobacterium* species in any of the three types of sample, but the first staining method has been found to be the most effective if the samples are blood samples or macerated tissue samples; the second staining method produces reasonable results on blood samples or macerated tissue samples but is not as effective as the first method. Preferably, both the first and second staining methods are preceded by the step of culturing the samples as hereinafter described, since this increases the number of dormant or cell wall deficient mycobacteria present, and thus makes them easier to detect.

IsoVitaleX® is a known proprietary preparation Formula*Per Litre

| | |
|---|---|
| Adenine | 1.0 g |
| p-Aminobenzoic Acid | 13.0 mg |
| L-Cysteine Hydrochloride | 25.9 g |
| L-Cystine | 1.1 g |
| Nicotinamide Adenine Dinucleotide | 0.25 g |
| Ferric Nitrate | 0.02 g |
| L-Glutamine | 10.0 g |
| Guanine Hydrochloride | 0.03 g |
| Thiamine Hydrochloride | 3.0 mg |
| Vitamin B12 | 0.01 g |
| Dextrose | 100.0 g |
| Thiamine Pyrophosphate | 0.1 g |

The third staining method is the preferred staining method for solid tissue samples.

First Staining Method.

The sample on the slide is stained using the alcohol free variant of the known Ziehl-Neelsen (ZN) stain using 20-25% sulphuric acid as a decolourising agent.

In the Ziehl-Neelsen staining method the slide is laid onto the surface of a heating element (typically heated to 65-70 degrees centigrade) and overlaid with Kinyoun Carbol Fuchsin to colour any mycobacteria present, which is washed off with water. The slide is then overlaid with the decolouriser; preferably, the decolouriser is sulphuric acid, most preferably 20%-25% sulphuric acid. The slide is again washed with water.

The slide is then overlaid with the counterstain, preferably 1% methylene blue (in distilled $H_2O$), or Loeffler's methylene blue for one to two minutes and then washed with water. The counterstain colours the background material to provide a contrast to the mycobacteria stained by the carbol fuchsin. The slide is then dried and examined under ×1000 oil immersion.

No alcohol is used in the decolourising agent or in the counterstain.

Second Staining Method.

In the second staining method, the slide is flooded with carbol fuchsin to colour any mycobacteria present, and allowed to stand at room temperature for 10 minutes. The slide is then washed in water and decolouriser and counterstained with Gabbett's methylene blue which combines a decolouriser and a counterstain together. The counterstain colours the background material to provide a contrast to the mycobacteria stained by the carbol fuchsin. The slide is again washed in water, and air dried.

Gabbett's methylene blue is prepared as follows:

methylene blue 1 gram, sulphuric acid (analytical reagent) 20 millilitres, absolute alcohol 30 millilitres, distilled water 50 millilitres.

Third Staining Method.

This is the preferred method for solid tissue samples.

Typically, this method would be used to analyse prepared tissue samples which had been prepared as formalin-fixed-paraffin embedded blocks prepared from large re-sections. Thin sections (typically 4 microns thick) are cut from each sample block for analysis.

With this type of sample, a necessary first step is to de-wax the sample; this is achieved by treating the sample with xylene for four minutes followed by ethanol for four minutes and then flushing with water until the sample is clear.

The sample is then immersed in a Ziehl-Neelsen solution of carbol-fuchsin for 35 minutes to colour any mycobacteria present, following which the sample is flushed with water until the sample is clear.

The sample is then decolourised to by immersing in a 30% solution of hydrochloric acid in isopropyl alcohol for one minute, and again flushing the sample with water until the sample is clear.

The sample is then treated with a 1% methylene blue solution for 10-60 seconds, to colour any background material and provide a contrast to the mycobacteria stained by the carbol fuchsin.

Figure 9:
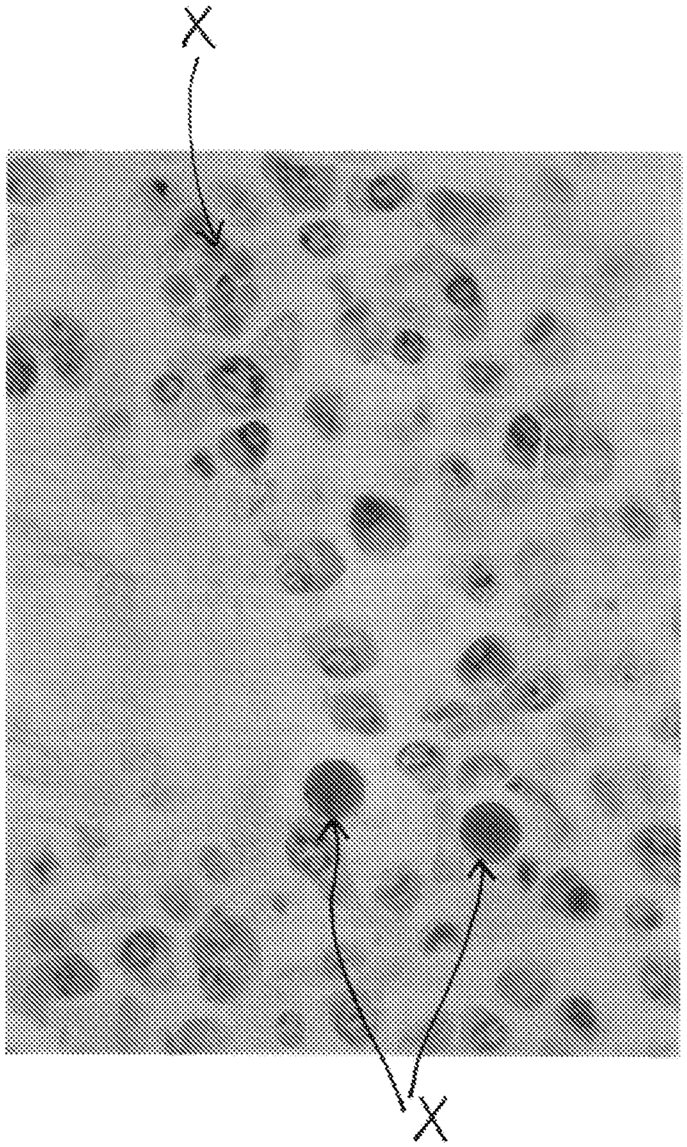
FIG. 9 is a photomicrograph of a solid tissue specimen stained in accordance with the third staining method.

FIG. 9 shows a solid tissue sample stained in accordance with the above described method. The mycobacteria present and coloured by the staining are indicated by arrows X.

The sample is then dehydrated, cleared and mounted in known manner.

The above method also could be used on larger tissue samples.

Preparation of Culture Medium.

For blood samples and macerated tissue samples, optimum results are obtained if the samples, before staining, are cultured to increase the number of dormant and cell wall deficient mycobacteria present.

The culture method of the present invention uses a novel culture medium, as described below.

A culture medium is prepared as detailed in steps 1-7 below. It should be noted that the medium must be sterile, but many ingredients would be destroyed by heat sterilisation, so they are filtered through a 0.22 micron filter to ensure sterility.

1. A base medium is prepared from:

Middlebrook's 7H9 broth—5.9 grams/litre

Bacto nutrient broth—1.25 grams/litre glycerol—2.0 millilitres/litre sodium chloride 4.0 grams/litre (preferred). Possible range 0-10.0 grams/litre.

The above ingredients are mixed together and made up to 1 litre with distilled water.

2. The base medium prepared in step 1 is sterilised at 121 degrees centigrade for 15 minutes. The sodium chloride can be introduced into the solution either before or after sterilisation.

3. A first additional preparation is made by mixing together the constituents listed below, stated in grams per litre of the final culture medium:—

| Constituent | Preferred Concentration | Acceptable range of concentration |
|---|---|---|
| Bovine serum albumin | 5 gram | 1 gram to 20 gram |
| Dextrose | 5 gram | 0.5 gram to 20 gram |
| Sucrose | 10 gram | 1 gram to 25 gram |
| Tryptophan | 0.5 gram | 0.01 gram to 4 gram |
| Glutamic acid | 0.5 gram | 0.01 gram to 5 gram |
| L alanine | 0.5 gram | 0.01 gram to 5 gram |
| Oleic acid | 0.05 millilitres | 0.01 millilitres to 2 millilitres |
| L lysine | 0.5 gram | 0.01 gram to 5 gram |
| L asparagine | 0.5 gram | 0.01 gram to 5 gram |
| Vitamin B12 | 0.1 gram | 0.0125 gram to 1 gram |

4. Preferably, the first additional preparation also includes the constituents listed in the table below, in grams per litre of the final culture medium:—

| Preferred Additional Constituents | Preferred Concentration | Acceptable range of concentration |
|---|---|---|
| Trehalose | 0.5 gram | 0.01 gram to 4 gram |
| D alanine | 0.5 gram | 0.01 gram to 5 gram |
| Putresciene | 0.5 gram | 0.01 gram to 5 gram |
| Cadavaerine | 0.5 gram | 0.01 gram to 0.5 gram |
| Cysteine | 0.5 gram | 0.01 gram to 0.5 gram |
| Sodium pyruvate | 4 gram | 0.01 gram to 10 gram |

5. A second additional preparation is made by mixing the constituents listed below, given per litre of the final culture medium:—

| Constituent | Preferred Concentration | Acceptable range of concentration |
|---|---|---|
| IsoVitaleX ® | 5 millilitres | 1 millilitres to 10 millilitres |
| Mycobactin J | 2 milligrams | 01 milligrams to 5 milligrams |
| PANTA medium | 15 millilitres per 200 millilitres | |

The culture media additive for growing fastidious microorganisms, such as Isovitalex®, which contains vitamin B12, thiamine pyrophosphate, L-glutamine, ferric nitrate, adenine, thiamine hydrochloride, guanine hydrochloride, L-cysteine hydrochloride, p-aminobenzoic acid, L-cystine, nicotinamide adenine dinucleotide, and dextrose. Mycobactin J, and antimicrobial supplement for culture media, such as PANTA®, which contains polymyxin B, amphotericin B, nalidixic acid, trimethoprim, and azlocillin are added to normal saline, (normal saline=9 grams/L in distilled water and sterilised) then dissolved and filtered through 0.22 micron sterile filter.

6. Foetal calf serum or guinea pig blood serum or sheep blood serum is prepared for use by inactivating the serum at 58 degrees centigrade for 30 minutes, and then filtering through a 0.22 micron sterile filter. Alternative known inactivation and sterilisation methods may be substituted.

7. To prepare the final culture medium, the base medium, and the first and second additional preparations are mixed to form a working medium and then foetal calf serum (or guinea pig blood serum or sheep blood serum) in a proportion 1%-10% by volume is added, to give the completed culture medium.

As noted above, the culture medium must be sterile. To ensure this, the first additional preparation may be sterilised by passing the mixture through a 0.22 micron filter before mixing with the second additional preparation and the serum. Alternatively, the first and second additional preparations may be mixed together, mixed with the inactivated serum and with the base medium (which has already been heat sterilised), and the final culture medium is then sterilised by passing through a 0.22 micron filter.

Each portion of culture medium may be used as a liquid culture medium or may be mixed into a standard agar base to form a solid jelly culture preparation on which samples may be cultured as described below.

Optionally, the culture medium may also contain egg yolk emulsion and/or cholesterol prepared as set out below.

Egg Yolk Emulsion

Sterile egg yolk is dissolved in distilled water using 50% by volume egg yolk of the volume of the water. The solution is then added to the culture medium in a proportion of 0.1%-3% by volume.

Cholesterol

Cholesterol powder is dissolved in ethanol, each 0.01 gram of cholesterol being dissolved in 2 millilitres ethanol, and is added at a rate of 0.001-1 grams of cholesterol per litre of culture medium.

Methods of Culturing Samples

Method 1

Citrated blood samples (i.e. blood samples collected using sodium citrate as an anticoagulant) are taken from the one or more people to be tested. Each blood sample is centrifuged at 3000 rpm for 10 minutes, and the buffy coat is harvested and inoculated into a series of containers each holding the liquid culture preparation described in steps 1-7 above.

Method 2

Citrated blood samples (i.e. blood samples collected using sodium citrate as an anticoagulant) are taken from the one or more people to be tested. Each blood sample is centrifuged at 3000 rpm for 10 minutes and the buffy coat is harvested and suspended in distilled water for two minutes. The sample is then shaken and spun at 12,000 rpm for 30 seconds, re-washed in distilled water and spun again. Each sample is then inoculated into a series of containers each holding the liquid culture preparation described in steps 1-7 above.

Advantageously, the distilled water used for each washing step has 0.5 percent N-acetyl L-cysteine added to it.

The effect of the additional treatment in method 2 is to cause lysis i.e. the breaking down of the outer membrane coatings of the mycobacteria in the sample. It is advantageous to cause lysis, because the mycobacteria in the sample are lodged inside the host's white cells, and the white cells need to be disrupted to release the mycobacteria. Further, causing lysis also effectively reduces/removes red cells from the sample, making it easier to see the stained mycobacteria.

Each of the samples inoculated onto the culture medium is then incubated at 36.5-39 degrees centigrade for between 8 and 30 days.

If a tissue sample is used instead of a blood sample then Method 3 is used:—the tissue sample is first macerated to homogenise it, decontaminated using known methods if necessary, and is then inoculated into the culture medium. From that point on, a tissue sample is treated in the same manner as the blood sample.

After at least eight days have elapsed, a glass sterile pipette or a plastic disposable pipette is used to draw approximately 50 μL (about one drop) from a cultured sample, and laid on a glass microscope slide. The slide is air dried and heat fixed.

Further Culturing Steps

Figure 2:
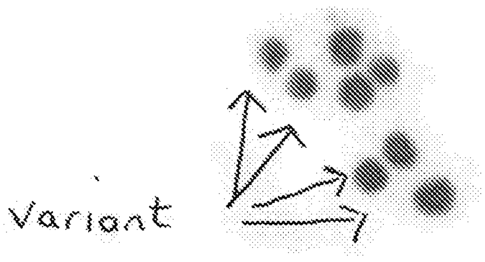
FIG. 2 is a photomicrograph of a cultured specimen after approximately 8 days culture.

If the staining step indicates growth of variant forms as shown in FIG. 2 then a sample of that culture is subcultured onto the culture medium. The subcultures are then cultured for a period of up to 3 months, and then one or more further samples are taken and stained as described above using any of the first, second or third staining methods.

Figure 3:
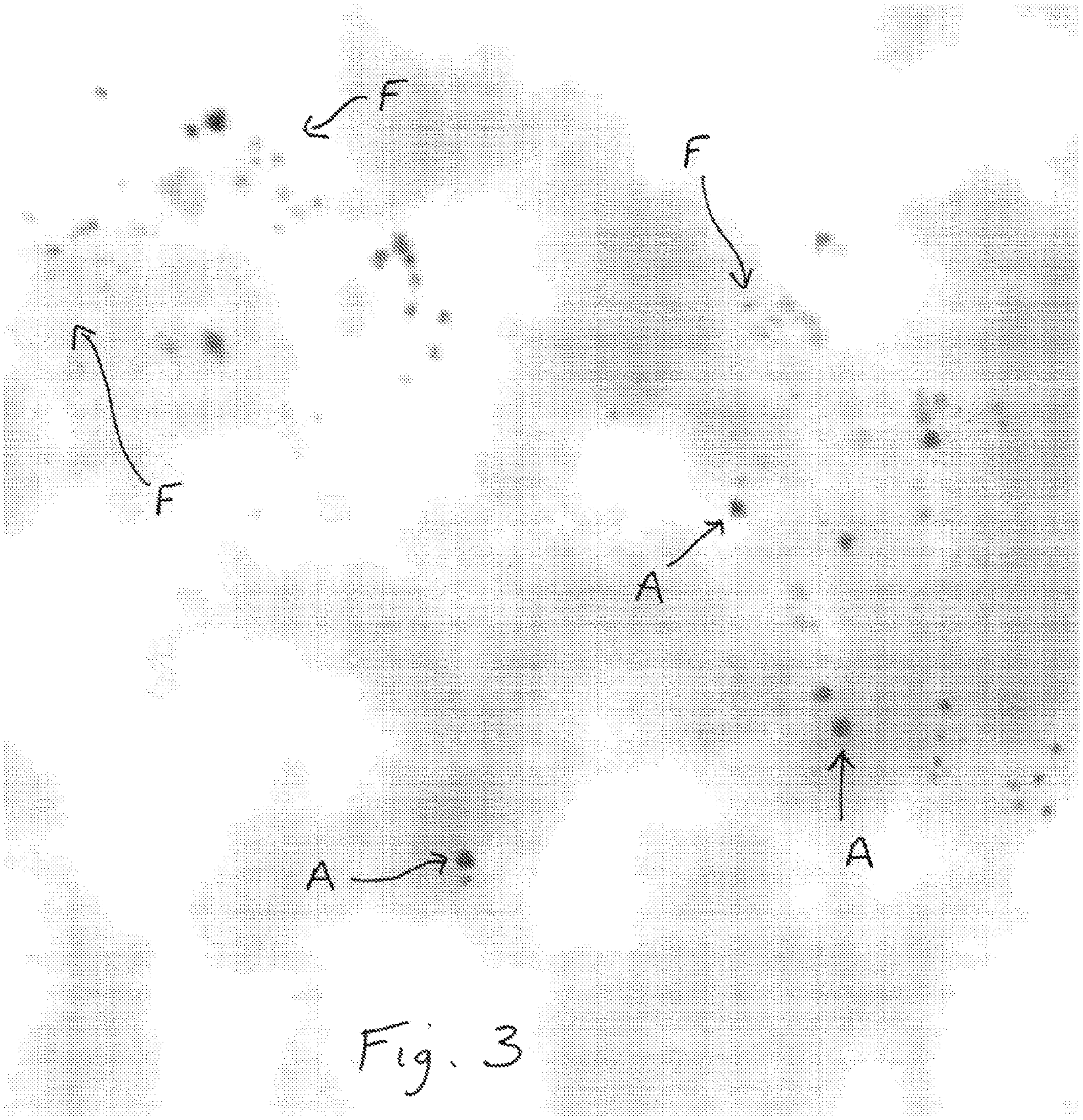
FIG. 3 is a photomicrograph of a cultured specimen at between 8 and 30 days culture.
Figure 4:
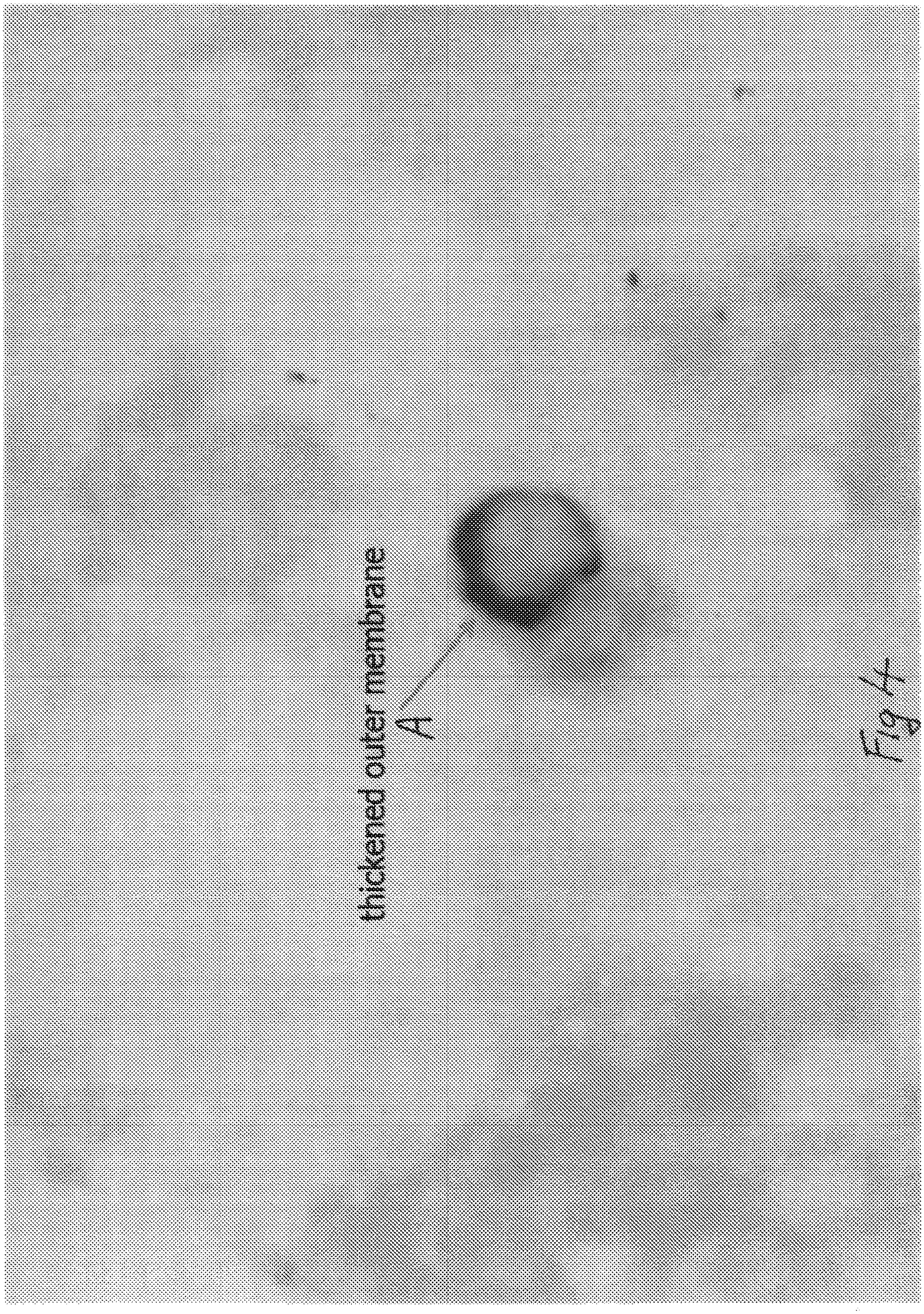
FIG. 4 is a photomicrograph of a cultured specimen showing the thickened outer membrane produced by the method of the present invention.

FIG. 3 shows the growths found at 8 and 30 day's examination. In FIG. 3, two forms are shown; one form (indicated by arrows F) is fragile and bursts to release its cell contents; the other form is viable and gradually develops a thickened outer membrane, as indicated by arrow A in FIGS. 3 and 4.

It is believed that a possible mechanism for the development of the thickened outer membrane is that the culture medium of the present invention assists the *Mycobacterium* of interest to put lipids on the inside of the outer membrane, gradually forming a coating of the outer membrane of the *Mycobacterium*. This thickened outer membrane becomes visible when the product is stained as described above, so that the *Mycobacterium* can be positively identified in the culture, for diagnostic or other purposes. It is believed that the culture medium of the present invention could be useful in assisting in the positive identification of a range of *Mycobacterium* species.

Figure 5:
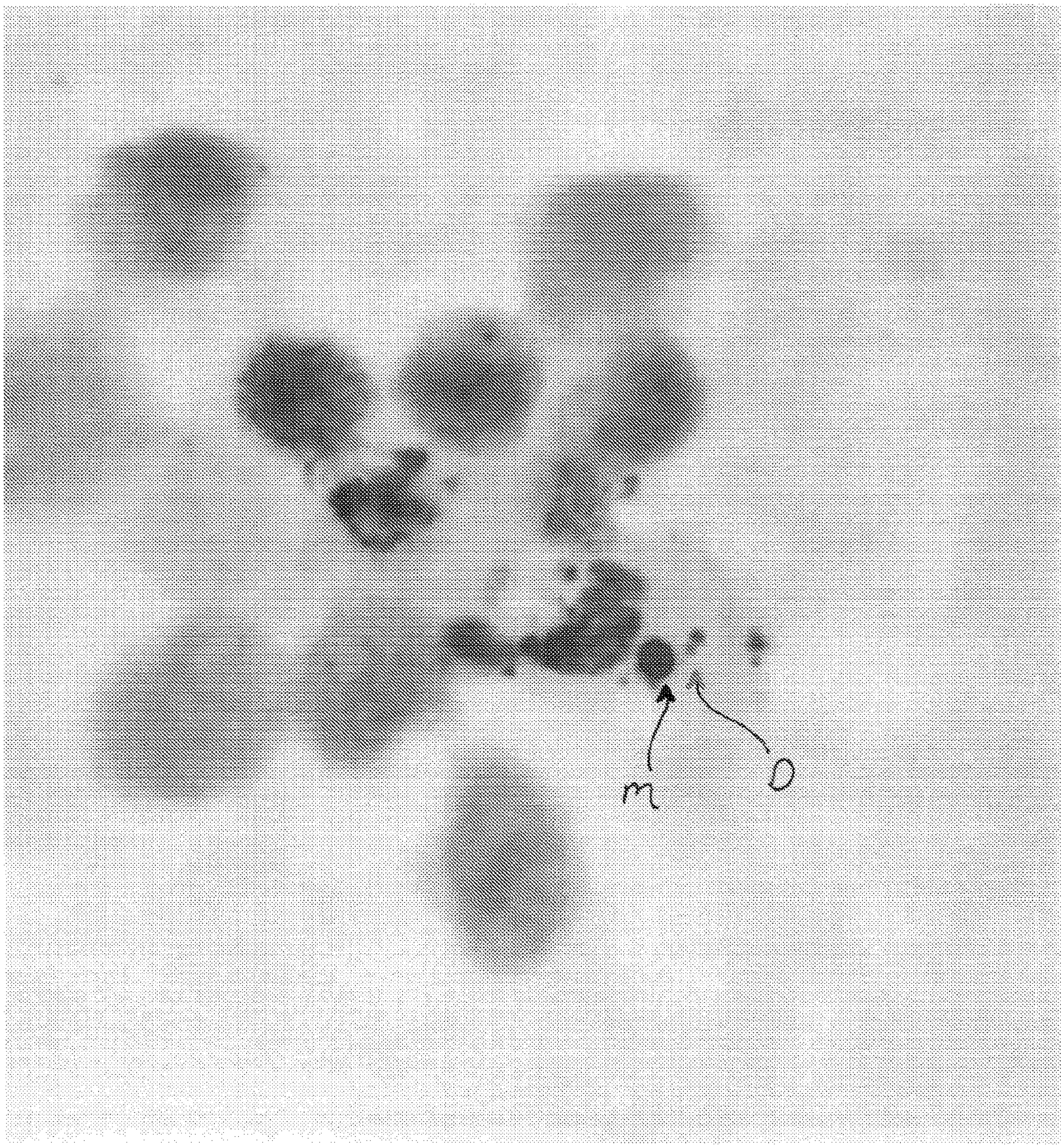
FIG. 5 is a photomicrograph of a cultured specimen showing the formation of "mother" and "daughter" forms.
Figure 6:
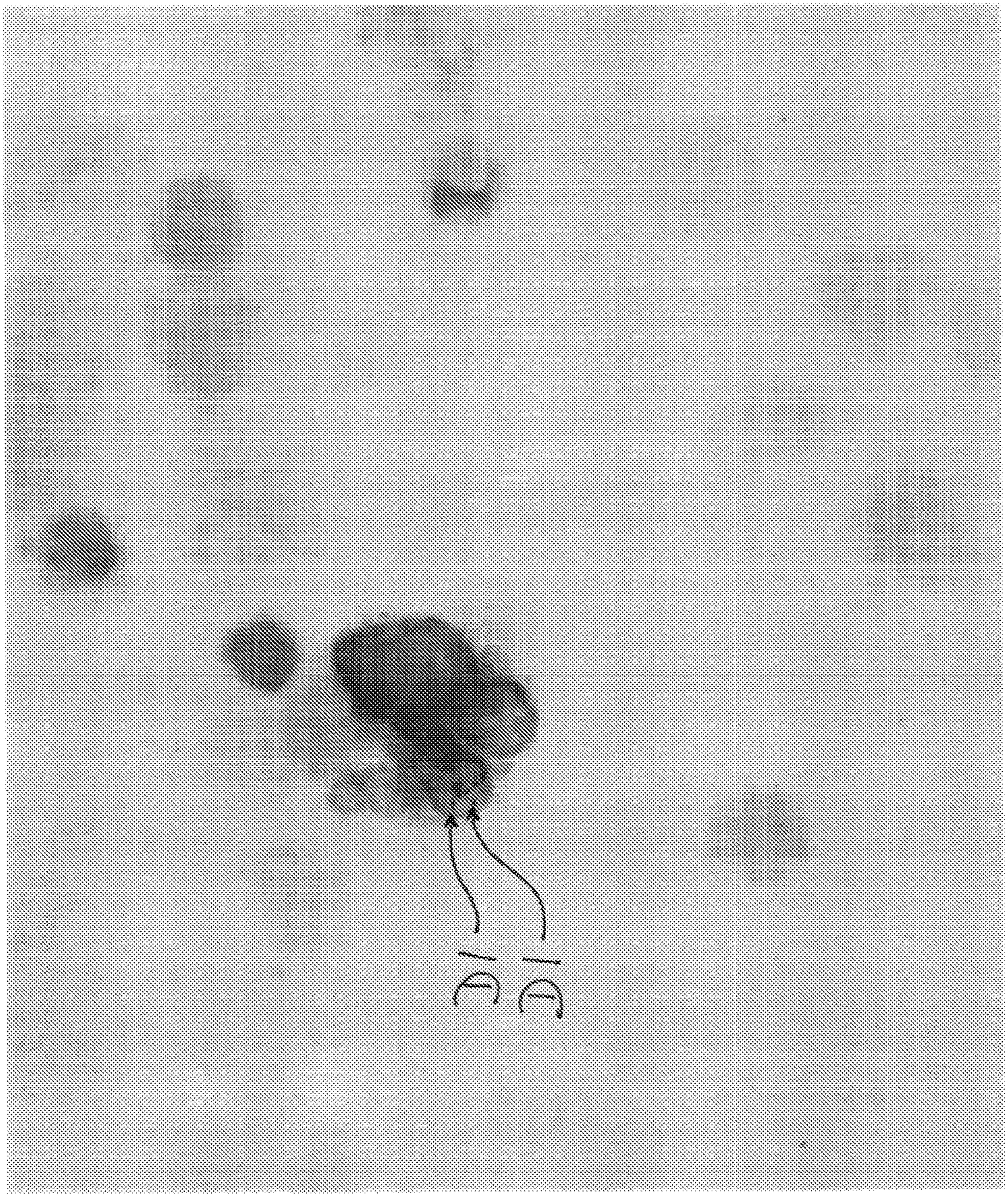
FIG. 6 is a photomicrograph of a cultured specimen showing a further development of the "mother" and "daughter" forms.

FIG. 5 shows the mother form (arrow M) and the daughter forms (arrows D). Following this stage, the daughter forms move to a transitional cell stage which, as indicated by arrows D1 in FIG. 6 appears to feature the production of lipid bodies within the cytoplasm; these bodies adhere to the membrane wall.

Figure 7:
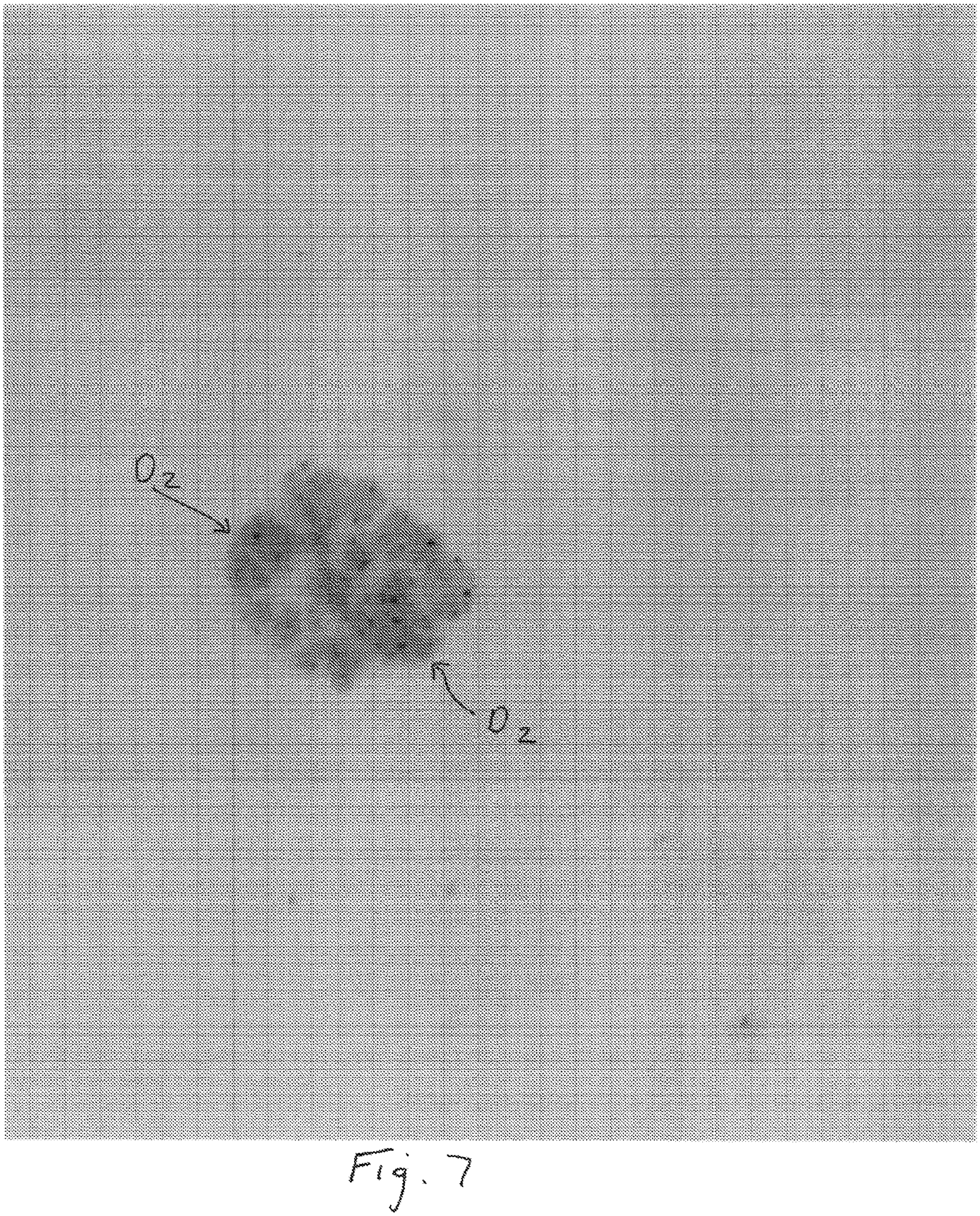
FIG. 7 is a photomicrograph of a cultured specimen showing transitional "daughter" cells.
Figure 8:
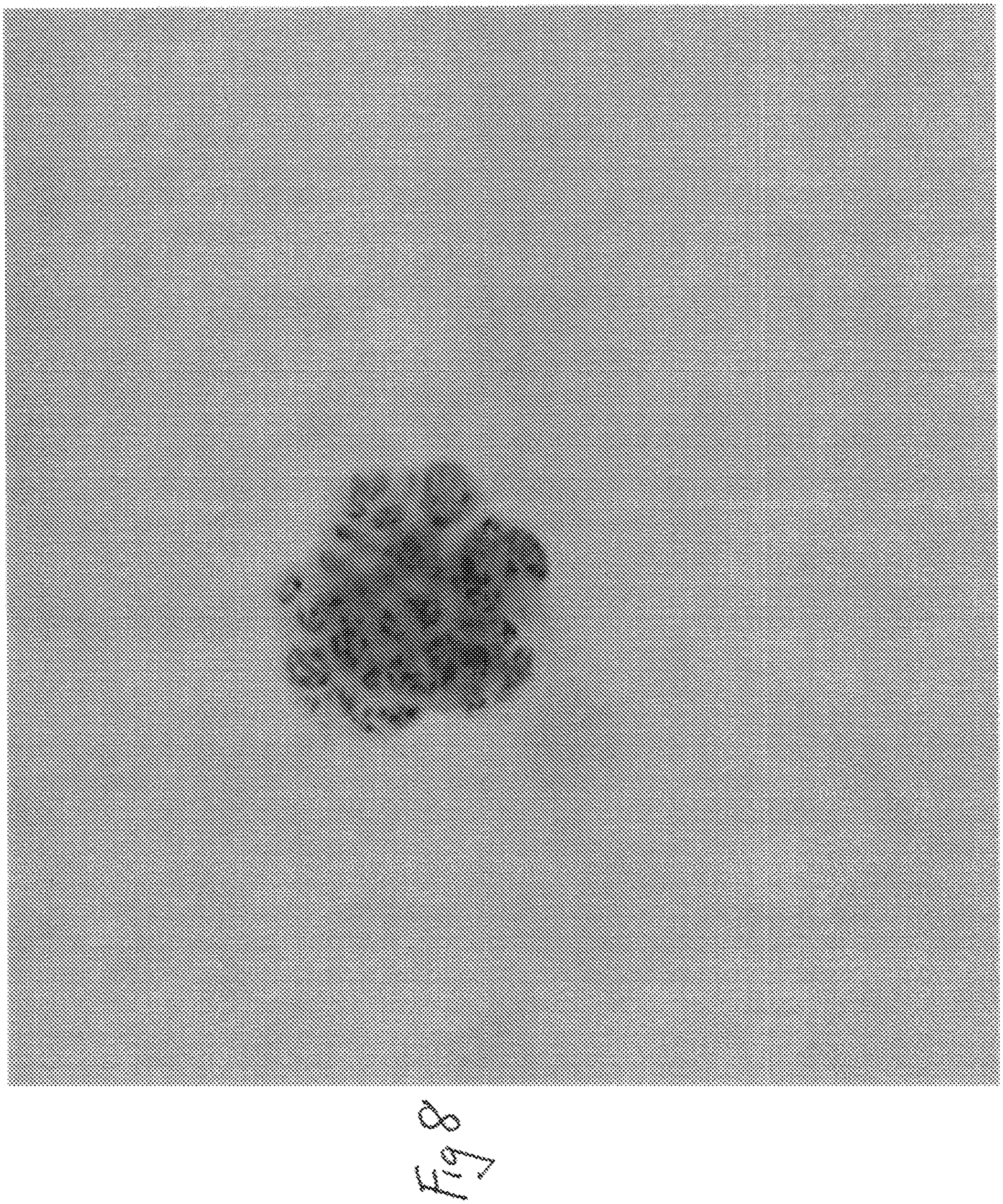
FIG. 8 is a photomicrograph of a cultured specimen showing the micro-colonies finally formed.

If cultures are incubated for an extended period (more than six months) then as shown in FIG. 7, transitional daughter cells indicated by arrows D2 strengthen the membrane, and lipid depositions consolidate. The transitional cells then either aggregate or proliferate and form micro-colonies as shown in FIG. 8. It is believed that the contents of the transitional cells and the contents of the daughter cells will be inflammatory triggers in the host.

Development of Pharmaceutical Animal Models

At present, no animal models are available for the detection and/or treatment of Crohn's disease or MAP. However, it is believed that a guinea pig model may be suitable, given that the guinea pig has a body temperature of 39° C. and is available free of any genetic manipulation. Ruminants, from which the species MAP originates, have body temperatures in the region of 39° C. rather than the 37° C. of the more popular animal model, the mouse. A further drawback is that mice developed for experimental purposes often have been subjected to gene manipulation. It is noted that guinea pigs have been used in tuberculosis research in some laboratories.

For animal pharmaceutical testing, particularly in Crohn's disease therapies, the Guinea pig may be a suitable model.

For an initial experiment, a total of four Guinea pigs were used:—two test Guinea pigs and two control Guinea pigs.

The test guinea pigs were fed an oral dose (approximately 1 millilitre) of organisms cultivated from the blood of two patients with Crohn's disease, at a dosage of $6\times10^8$ organisms per millilitre.

The dose was suspended in 1 millilitre of ultra-heat treated milk; pasteurised egg yolk could be substituted for the milk. The suspension liquid or egg yolk is protective of the bacteria as they transit the stomach region.

The guinea pigs were tested weekly for 4 weeks to ascertain uptake in the blood. The culture medium described above was used for the blood cultures.

The monitoring ceased at the four-week point. At 12 weeks the animals were sacrificed Cultures of samples from the organs and lymph nodes showed the presence of cell-wall-deficient mycobacteria present in both test animals and none in controls.

The tissue samples from the sacrificed guinea pigs were prepared as follows:—the samples were mechanically macerated and were placed in the culture medium described above. Where there was a chance of contamination, samples were decontaminated prior to culture.

Samples were cultured at 37° C. and 39° C. for an extended period, examined microscopically and subcultured periodically into the culture medium. Changes in the cell wall deficient mycobacteria were noted. Staining method 1 described above was used to stain these samples before microscopic examination.

Further solid tissue samples from the sacrificed guinea pigs were checked for inflammation in the tissue, using histological staining methods of known type; this was to determine whether or not inflammation was being treated successfully by the treatment.

The tests to date have of course been very small scale, but it is believed that they are sufficient to show that a Guinea pig model would be suitable for evaluating treatment methods.

Typically, to evaluate a treatment method, the Guinea pigs would have a Crohn's-like inflammation induced, and then a therapy given to selected animals e.g. a suitable antibiotic treatment, and the treated animals and non-treated (control) animals would be evaluated at intervals to see whether or not the treatment was succeeding in overcoming the condition.

Another possible evaluation would involve placing one group of guinea pigs on a selected treatment therapy, with an untreated control group, and then inducing in both groups a Crohn's' like inflammation. Both the treated and untreated groups would then be evaluated at intervals to see whether the treatment therapy had been successful in preventing the treated group from developing the condition.

It should be noted that the techniques provided by the present invention permit humane monitoring of groups of test animals, in that the monitoring can be conducted using blood samples rather than necessarily having to sacrifice the test animals.

The above described third staining method was used to examine ileal tissue samples taken from each of the following groups:

1. 22 human patients who have been diagnosed with Crohn's disease;
2. 15 human patients who have been assessed as free from Crohn's disease.

For each patient of the two groups, examination of prepared tissue sections of resected ileal tissue, treated as set out in the third staining method described above, indicated the presence of cell wall deficient mycobacteria in all 22 of the diagnosed Crohn's patients but in none of the 15 patients assessed as free from Crohn's disease.

However, in the event that colonic biopsies are performed on Crohn's patients, tissue extracted in the biopsy (which is in the form of very small tissue particles) preferably is cultured in the culture medium as described above, and then is stained using staining method 1.

As a general comment on the information provided by the above described testing techniques, it should be noted that the higher the number of target mycobacteria found in a particular sample, the more severe the corresponding disease or condition.

The invention claimed is:

1. A sterilized culture medium for growing dormant or cell wall deficient forms of bacterial cells belonging to *Mycobacterium* species, said sterilized culture medium comprising:

I) a base medium containing: 5.9 gm/L Middlebrook's 7H9 broth, 1.25 gm/L nutrient broth, 2.0 ml/L glycerol, and 0 gm/L to 10.0 gm/L sodium chloride, which are made up to 1 liter with distilled water to form a mixture, wherein said mixture is sterilized by heating, and wherein said sodium chloride may be added to said mixture before or after said mixture is sterilized by heating;

II) a first additional preparation containing components as listed below:

| | |
|---|---|
| Bovine serum albumin | 1 gm/L to 20 gm/L |
| Dextrose | 0.5 gm/L to 20 gm/L |
| Sucrose | 1 gm/L to 25 gm/L |
| Tryptophan | 0.01 gm/L to 4 gm/L |
| Glutamic acid | 0.01 gm/L to 5 gm/L |
| L-alanine | 0.01 gm/L to 5 gm/L |
| L-lysine | 0.01 gm/L to 5 gm/L |
| L-asparagine | 0.01 gm/L to 5 gm/L |
| Vitamin B12 | 0.0125 gm/L to 1 gm/L |
| Trehalose | 0.01 gm/L to 4 gm/L |
| D-alanine | 0.01 gm/L to 5 gm/L |
| Sodium pyruvate | 0.01 gm/L to 10 gm/L |

plus 0.01 ml/L to 2 ml/L of oleic acid;

III) a second additional preparation made by dissolving in a saline solution 1 ml to 10 ml of a culture medium additive, 0.1 mg to 5 mg of Mycobactin J, and an antimicrobial supplement, wherein said culture medium additive contains vitamin B12, thiamine pyrophosphate, L-glutamine, ferric nitrate, adenine, thiamine hydrochloride, guanine hydrochloride, L-cysteine hydrochloride, p-aminobenzoic acid, L-cystine, nicotinamide adenine dinucleotide, and dextrose, wherein said antimicrobial supplement contains polymyxin B, amphotericin B, nalidixic acid, trimethoprim and azlocillin, and wherein said antimicrobial supplement is present at 15 ml per 200 ml of said sterilized culture medium; and IV) a heat-inactivated serum selected from the group consisting of: fetal calf serum, guinea pig blood serum, and sheep blood serum; wherein said sterilized culture medium is prepared by mixing said base medium, said first additional preparation and said second additional preparations to form a working medium and adding said heat-inactivated serum to said working medium in a proportion of 1%-10% by volume, and wherein said first additional preparation, said second additional preparation, and said heat-inactivated serum are filtered for sterility.

2. The sterilized culture medium as claimed in claim 1, further including an egg yolk emulsion prepared by dissolving an egg yolk in distilled water using 50% by volume of said egg yolk and 50% by volume of said distilled water, wherein said egg yolk emulsion is added to said sterilized culture medium in a proportion of 0.1%-3% by volume.

3. The sterilized culture medium as claimed in claim 1, further including cholesterol dissolved in ethanol, wherein each 0.01 gram of said cholesterol is dissolved in 2 milliliters of said ethanol and is added to said sterilized culture medium in a range from 0.001 gram to 1 gram of cholesterol per liter of said sterilized culture medium.

4. The sterilized culture medium as claimed in claim 1, wherein said first additional preparation includes,

| | |
|---|---|
| Bovine serum albumin | 5 gm/l |
| Dextrose | 5 gm/l |
| Sucrose | 10 gm/l |
| Tryptophan | 0.5 gm/l |
| Glutamic acid | 0.5 gm/l |
| L-alanine | 0.5 gm/l |
| Oleic acid | 0.05 ml/l |
| L-lysine | 0.5 gm/l |
| L-asparagine | 0.5 gm/l |
| Vitamin B12 | 0.1 gm/l |

5. The sterilized culture medium as claimed in claim 1, wherein within said second additional preparation, said culture medium additive is present at 5 ml/L, said Mycobactin J is present at 2 mg/L, and said antimicrobial supplement is present at 15 ml per 200 ml of said sterilized culture medium.

6. The sterilized culture medium as claimed in claim 1, wherein said first additional preparation also contains,

| | |
|---|---|
| Putrescine | 0.01 gm/l to 5 gm/l |
| Cadaverine | 0.01 gm/l to 0.5 gm/l |
| Cysteine | 0.01 gm/l to 0.5 gm/l |

7. The sterilized culture medium as claimed in claim 6, wherein said first additional preparation includes,

| | |
|---|---|
| Trehalose | 0.5 gm/l |
| D--alanine | 0.5 gm/l |
| Putrescine | 0.5 gm/l |
| Cadaverine | 0.5 gm/l |
| Cysteine | 0.5 gm/l |
| Sodium pyruvate | 4 gm/l |

8. The sterilized culture medium as claimed in claim 6, further including an egg yolk emulsion prepared by dissolving an egg yolk in distilled water using 50% by volume of said egg yolk and 50% by volume of said distilled water, wherein said egg yolk emulsion is added to said sterilized culture medium in a proportion of 0.1%-3% by volume.

9. The sterilized culture medium as claimed in claim 8, further including cholesterol dissolved in ethanol, wherein each 0.01 gram of said cholesterol is dissolved in 2 milliliters of said ethanol and is added to said sterilized culture medium in a range from 0.001 gram to 1 gram of cholesterol per liter of said sterilized culture medium.

10. The sterilized culture medium as claimed in claim 9, wherein said first additional preparation includes,

| | |
|---|---|
| Bovine serum albumin | 5 gm/l |
| Dextrose | 5 gm/l |
| Sucrose | 10 gm/l |
| Tryptophan | 0.5 gm/l |
| Glutamic | 0.5 gm/l |

-continued

| | |
|---|---|
| acid | |
| L-alanine | 0.5 gm/l |
| Oleic acid | 0.05 ml/l |
| L-lysine | 0.5 gm/l |
| L-asparagine | 0.5 gm/l |
| Vitamin B12 | 0.1 gm/l |
| Trehalose | 0.5 gm/l |
| D-alanine | 0.5 gm/l |
| Sodium pyruvate | 4 gm/l |

11. The sterilized culture medium as claimed in claim 10, wherein said first additional preparation further contains,

| | |
|---|---|
| Putrescine | 0.5 gm/l |
| Cadaverine | 0.5 gm/l |
| Cysteine | 0.5 gm/l |

12. The sterilized culture medium as claimed in claim 11, wherein within said second additional preparation, said culture medium additive is present at 5 ml/L, said Mycobactin J is present at 2 mg/L, and said antimicrobial supplement is present at 15 ml per 200 ml of said sterilized culture medium.

* * * * *